(12) United States Patent
Hommeltoft

(10) Patent No.: US 7,077,950 B2
(45) Date of Patent: Jul. 18, 2006

(54) CONTINUOUS PROCESS FOR THE REMOVAL OF WATER FROM A HYDROCARBON STREAM

(75) Inventor: Sven Ivar Hommeltoft, Hillerød (DK)

(73) Assignee: Haldor Topsoe A/S, Lyngby (DK)

( * ) Notice: Subject to any disclaimer, the term of this patent is extended or adjusted under 35 U.S.C. 154(b) by 657 days.

(21) Appl. No.: 10/406,216

(22) Filed: Apr. 4, 2003

(65) Prior Publication Data

US 2003/0199723 A1 Oct. 23, 2003

(30) Foreign Application Priority Data

Apr. 18, 2002 (DK) ............................... 2002 00578

(51) Int. Cl.
*C10G 33/04* (2006.01)

(52) U.S. Cl. ...................... 208/187; 208/188; 208/289; 585/833; 585/846; 585/858; 585/859

(58) Field of Classification Search ................. 208/187, 208/188, 289; 585/833, 846
See application file for complete search history.

(56) References Cited

U.S. PATENT DOCUMENTS 3,793,187 A 2/1974 Marx et al.
4,484,933 A 11/1984 Cohen

*Primary Examiner*—Tam M. Nguyen
(74) *Attorney, Agent, or Firm*—Dickstein Shapiro Morin & Oshinsky LLP

(57) ABSTRACT

Process for the continuous drying of a hydrocarbon stream at a temperature being effective in drying the stream with an ionic liquid drying agent comprising a salt of sulphuric acid being in liquid or melted form at the drying temperature.

6 Claims, No Drawings

CONTINUOUS PROCESS FOR THE REMOVAL OF WATER FROM A HYDROCARBON STREAM

BACKGROUND OF THE INVENTION

The present invention relates to a process for removing water from a hydrocarbon process stream. When processing hydrocarbon streams in processes such as isobutane alkylation in which the catalyst is sensitive to water, it is necessary to dry the hydrocarbon stream to minimise the effect of the water on the catalyst. Drying of a hydrocarbon stream is typically achieved by passing the stream over a solid absorbent such as alumina or molecular sieve. Subsequently, the absorbent is regenerated by heating it in a stream of inert gas to a temperature, which is substantially above the temperature of absorption i.e. 250–300° C. This method is effective for drying down to water levels below 10 ppm in the hydrocarbon stream. The disadvantage of this approach is that the absorption and the desorption is done under substantially different conditions in the same vessel. Consequently, the vessel has to be taken out of drying service for regeneration making the operation discontinuous. In addition the system including the adsorption vessel has to be designed for substantial changes in temperature and sometimes also in pressure to accommodate the different conditions for drying and regeneration.

Wash of hydrocarbon stream with a saturated solution of a highly soluble salt such as calcium chloride may be used for drying. This method does not dry the hydrocarbon stream efficiently.

Strong acids such as concentrated sulphuric acid are efficient drying agents, but such material is too reactive for many drying operations. Sulphuric acid may for instance act either as an oxidising agent oxidising the hydrocarbons or as acid catalyst catalysing undesirable reactions.

According to the present invention an improved process for the continuous drying of a hydrocarbon stream at a temperature being effective in drying the stream comprises contacting the stream with an ionic liquid drying agent comprising a salt of sulphuric acid being in liquid or melted form at the drying temperature.

Extraction of the hydrocarbon stream with a dry ionic liquid made from sulphuric acid by addition of up to one equivalent of one or more basic nitrogen compounds including amines, such as diethylmethyl amine or triethanolamine or a basic heterocyclic compound, e.g. 1-butyl pyrollidine, provides a convenient and efficient method for continuous drying of a hydrocarbon stream. The addition of the basic nitrogen compound lowers the activity of the sulphuric acid in such a way that undesired side reactions being a problem if sulphuric acid is used are avoided. Such undesired side reactions may for instance be oxidation or the hydrocarbons by the sulphuric acid acting as an oxidising agent or it may be acid catalysed reactions induced by the high acidity of sulphuric acid.

The extraction may be performed in a continuous counter-flow extraction operation in an extraction column or other liquid-liquid extraction equipment or it may be achieved using either a co-flow column or a simple mixer separator set. In the later embodiment of the invention a stream comprising the liquid sulphate drying agent phase and another stream of the hydrocarbon phase are contacted in a mixer, which may be a static mixed, and the two phases are subsequently separated again in a separator. The mixer-separator embodiment provides for a relatively inexpensive way to contact the two liquid phases.

The liquid sulphate drying agent may be continuously regenerated by drying in a subsequent step of stripping off the water at elevated temperature in a stripping column using an inert stripping agent such as a hydrocarbon or nitrogen or air. The thus regenerated drying agent is then recycled to the extraction step.

EXAMPLE 1

A stream of heptane saturated with water was contacted with a dry ionic sulphate (diethylmethylammonium bisulphate, $Et_2MeNH^+.HSO_4^-$) in a mixer at a temperature of 20° C. in a continuous operation. The ionic liquid was charged at a feed rate of 325 g/h to a mixer and the hydrocarbon stream was charged at a feed rate of 294 g/h to the same mixer. In order to ensure efficient mixing the mixer was equipped with an effluent recycle loop. The mixer consisted of six 3 mm Sulzer mixer elements and the effluent recycle flow over the mixer was adjusted to give a pressure drop over the mixer of approximately 0.3 bar. The wetted ionic liquid withdrawn from the mixer was passed to top of a stripping column in which the ionic liquid was dried by stripping in counter flow with a stream of super-heated heptane (175° C.) before being withdrawn at the bottom of the stripping column and returned to the mixer loop. The wet ionic liquid was charged to the top at a feed rate of 325 g/h at ambient temperature and the dried ionic liquid was withdrawn from the bottom of the stripping column and returned to the hydrocarbon contact column. Heptane vapour was fed to the stripping column at approximately 500 g/h. The stripping column was 0.4 m high with ID=30 mm and filled with 300 ml 4×4 mm stainless steel Raschig-rings.

| 1. Contact Column (Hydrocarbon drying) | |
|---|---|
| Hydrocarbon flow (feed) , g/h | 294 |
| Ionic liquid flow, g/h | 325 |
| Before treatment | 80 |
| Wet hydrocarbon feed, ppm water | |
| After treatment (product) | 8 |
| Dry hydrocarbon product, ppm water | |
| Hydrocarbon feed temperature ° C. | 20 |
| Ionic liquid feed temperature ° C. | 20 |
| Hydrocarbon/Ionic liquid rate | 0.9 |
| 2. Stripping column (Ionic liquid drying) | |
| Ionic liquid flow, g/h | 325 |
| Heptane flow, g/h | approximately 500 |
| Ionic liquid feed temperature ° C. | (preheated to approximately 100° C.) |
| Heptane feed temperature ° C. | 98 |

EXAMPLE 2

This experiment was performed in the same equipment as used in Example 1 but instead of diethylmethylammonium bisulphate, $Et_2MeNH^+.HSO_4^-$, a mixture of 164 g $Et_2MeNH^+$ $HSO_4^-$ and 83 g 96% $H_2SO_4$ (1:1 molar ratio) was used.

| 1. Contact Column | |
|---|---|
| Hydrocarbon flow (feed), g/h | 514 |
| Ionic liquid flow, g/h | 325 |
| Before treatment<br>Wet hydrocarbon feed, ppm water | 49 |
| After treatment (product)<br>Dry hydrocarbon product, ppm water | 7 |
| Hydrocarbon feed temperature ° C. | 20 |
| Ionic liquid feed temperature ° C. | 20 |
| Hydrocarbon/Ionic liquid rate | 1.6 |
| 2. Stripping column | |
| Ionic liquid flow, g/h | 409 |
| Heptane flow, g/h | Approximately 500 |
| Before treatment<br>Wet ionic liquid, ppm water | 104 |
| After treatment<br>Dry ionic liquid, ppm water | 66 |
| Ionic liquid feed temperature ° C. | (Preheated to approximately 100° C.) |
| Stripping temperature ° C. | 175 |

The invention claimed is:

1. Process for the continuous drying of a hydrocarbon stream at a temperature being effective in drying the stream with an ionic liquid drying agent comprising a salt of sulphuric acid being in liquid or melted form at the drying temperature.

2. Process according to claim 1, wherein the hydrocarbon stream is dried with the ionic liquid in a static mixer.

3. Process according to claim 1, wherein the ionic liquid drying agent is regenerated by drying in stripping column in counter flow with a heated gaseous inert stripping agent.

4. Process according to claim 3, wherein the inert stripping agent is a condensable hydrocarbon.

5. Process according to claim 1, wherein the salt of sulphuric acid contains a basic nitrogen compound.

6. Process according to claim 1, wherein the salt of sulphuric acid is a trialkylammonium salt and/or triethanolammonium salt.

* * * * *